United States Patent
Oppelt et al.

[11] Patent Number: 5,917,414
[45] Date of Patent: Jun. 29, 1999

[54] BODY-WORN MONITORING SYSTEM FOR OBTAINING AND EVALUATING DATA FROM A PERSON

[75] Inventors: Arnulf Oppelt, Spardorf; Manfred Pfeiler, Erlangen, both of Germany

[73] Assignee: Siemens Aktiengesellschaft, Munich, Germany

[21] Appl. No.: 08/911,459

[22] Filed: Aug. 14, 1997

[30] Foreign Application Priority Data

Sep. 13, 1996 [DE] Germany ............... 196 37 383

[51] Int. Cl.⁶ .................................... G08B 23/00
[52] U.S. Cl. ................... 340/573.1; 340/573.3; 600/301
[58] Field of Search ............... 340/573, 572, 340/825.36, 825.49, 557, 573.1, 573.3, 573.7, 572.1; 128/668, 696, 630, 639, 903; 600/301

[56] References Cited

U.S. PATENT DOCUMENTS

| | | | |
|---|---|---|---|
| 4,117,834 | 10/1978 | Mc Partland et al. | 600/595 |
| 4,782,836 | 11/1988 | Alt | 607/19 |
| 4,827,943 | 5/1989 | Bornn et al. | 128/668 |
| 4,838,275 | 6/1989 | Lee | 600/483 |
| 5,036,861 | 8/1991 | Sembrowich et al. | 128/763 |
| 5,153,584 | 10/1992 | Engira | 340/573 |
| 5,335,664 | 8/1994 | Nagashima | 340/573 |
| 5,387,229 | 2/1995 | Poore | 607/18 |
| 5,532,680 | 7/1996 | Ousborne | 340/557 |
| 5,682,882 | 11/1997 | Lieberman | 600/301 |
| 5,701,894 | 12/1997 | Cherry et al. | 600/301 |
| 5,724,025 | 3/1998 | Tavori | 340/573 |

FOREIGN PATENT DOCUMENTS

OS 44 37 538  5/1995  Germany .
2 205 648  12/1988  United Kingdom .

*Primary Examiner*—Jeffery A. Hofsass
*Assistant Examiner*—Van T. Trieu
*Attorney, Agent, or Firm*—Hill & Simpson

[57] ABSTRACT

A body-worn monitoring system for obtaining and evaluating data from a person includes at least one sensor carried by the person to be monitored, and an evaluation unit worn by the person to be monitored which is supplied from a signal from the sensor. The evaluation unit either independently, or in communication with a remote computer, evaluates the data and initiates the generation of a message which is communicated to the monitored person by the evaluation unit. If data which is typical of the daily behavior pattern of the person fails to arrive, the person can be reminded of the necessity of undertaking a particular activity.

14 Claims, 2 Drawing Sheets

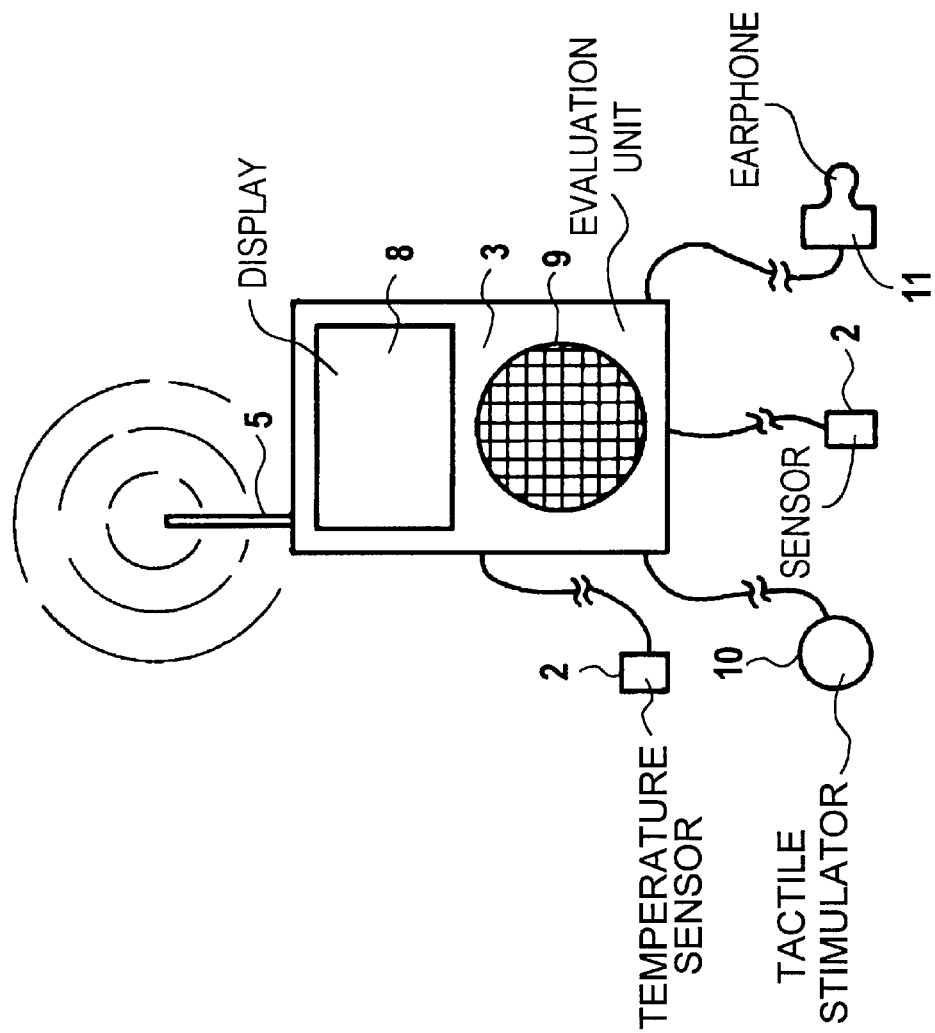
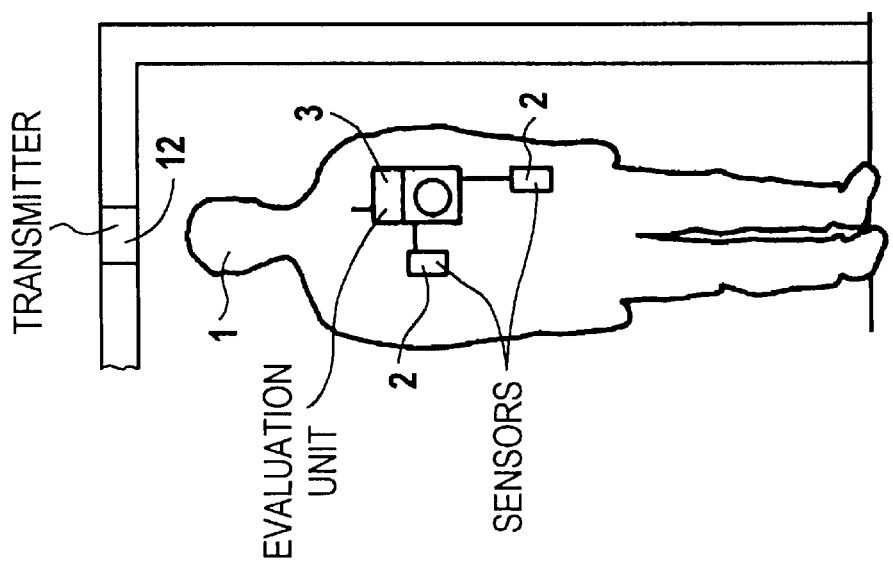

BODY-WORN MONITORING SYSTEM FOR OBTAINING AND EVALUATING DATA FROM A PERSON

BACKGROUND OF THE INVENTION

1. Field of the Invention

The present invention is directed to a monitoring system of the type worn on the body of a person, for obtaining and evaluating data from that person.

2. Description of the Prior Art

Certain persons exhibiting slightly diminished mental capacity, such as some categories of senior citizens, require substantially constant monitoring of their physical condition, and may need to be reminded of certain activities which must be undertaken either on a periodic basis or on an "as needed" basis. If such monitoring and reminding is done by another person, such as a nurse or an attendant, this can be highly time consuming, and therefore expensive.

For non-invasive glucose monitoring of a patient, U.S. Pat. No. 5,036,861 discloses a system including sensors which are placed on the body surface, with signals being supplied from the sensors to an evaluation unit which is worn on the body. This known apparatus, however, is not suitable for monitoring subjects having diminished mental capacity. German OS 44 37 538 and British Specification 2 205 648 disclose the wireless transmission of bio-signals for various purposes. These known systems are also not suitable for monitoring and reminding persons having reduced mental capacity.

SUMMARY OF THE INVENTION

It is an object of the present invention to provide an apparatus for acquiring data representing a condition of a person and for automatically evaluating this data so as to generate an automatic reminder to the person to undertake activities relating to the monitored data.

It is a further object of the present invention to provide such an apparatus which is capable of generating an alarm if data which are typical of the normal course of a day fail to arrive.

The above objects are achieved in accordance with the principles of the present invention in a body-worn monitoring system having a number of motion sensors which are carried on the body of a person whose condition is to be monitored, the motion sensors generating signals which are supplied to an evaluation unit which is also worn by the monitored person. The evaluation unit includes a trainable system and evaluates the data from the motion sensors in order to identify the current condition of the monitored person. The result of the evaluation can be communicated to the monitored person optically and/or acoustically.

The motion sensors can interact with other components which are installed at various locations in the living environment of the monitored person, so that the location of the person can be identified at all times. Other types of sensors can also be used such as temperature sensors which monitor environmental temperature.

The evaluation unit can be programmed and/or trained so as to take the time of day into consideration in evaluating the signals from the sensors.

The result of the evaluation, in addition to being communicated to the monitored person, can be transmitted, such as by wireless transmission, to a remote monitoring location. Another alternative is for the evaluation unit to be connectable to a remote monitoring station via the telephone network.

DESCRIPTION OF THE DRAWINGS

FIG. 1 is a schematic illustration of a body-worn monitoring system constructed in accordance with the principles of the present invention.

FIG. 2 shows details of the evaluation unit in the inventive body-worn monitoring system.

DESCRIPTION OF THE PREFERRED EMBODIMENTS

Figure 3:
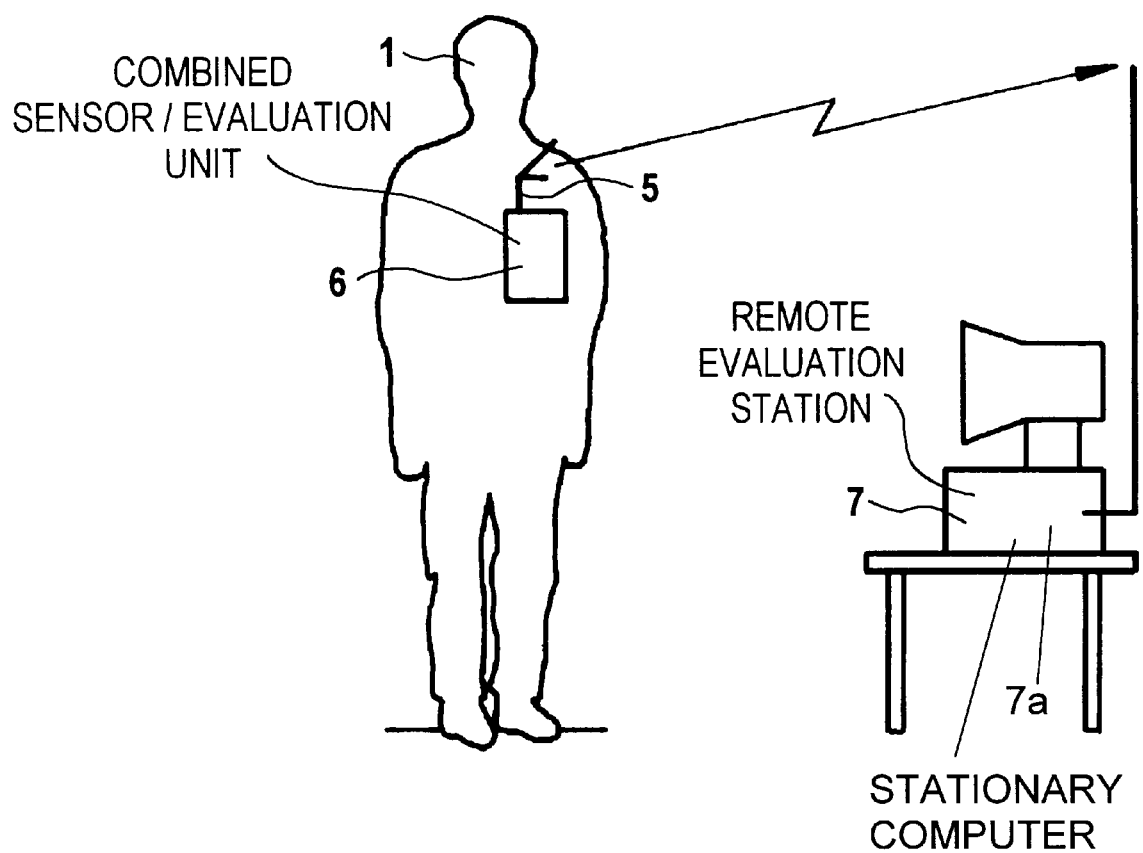
FIG. 3 shows a further embodiment of a body-worn monitoring system, together with a remote evaluation station.

FIG. 1 shows a person 1 who requires monitoring, wearing a number of body-proximate sensors 2. The body-proximate sensors 2 need not be directly connected to the body of the person 1 but can be worn, for example, on the clothing of the person 1. The person 1 also wears an evaluation unit 3 connected to the sensors 2. The evaluation unit 3 may be trainable, i.e., it may include a neural network.

The sensors 2 may independently monitor a condition of the person 1, such as the temperature of the environment in which the person 2 is currently located.

If necessary, however, the sensors 2 can be worn directly on the body of the person 1, in which case various types of physiological information can be obtained.

Another alternative is for the sensors 2 to interact with a number of transmitters which are positioned at various locations around the living environment of the person 1. One such transmitter 12 is shown in FIG. 1 located in a doorway. The signals received by the sensors 2, dependent on the strength or some other attribute of the signals received from one or more transmitters 12, then are evaluated in the evaluation unit 3 to identify the position of the person 1 in the living environment.

As shown in FIG. 2, the evaluation unit 3 includes an antenna 5 which can be used to transmit information to a remote monitoring location. The transmitted information can either be the raw data produced by the sensors 2, or the result of the evaluation which takes place within the evaluation unit 3.

The evaluation unit 3 also has a display 8 and a speaker 9, for optically and/or acoustically providing information to the person 1 as a result of the evaluation of the data from the sensors 2 undertaken in the evaluation unit 3. The evaluation unit 3 can also be provided with a tactile stimulator 10, if necessary, if the monitored person 1 does not respond well to acoustical or optical stimuli. Instead of or in addition to the speaker 9, the evaluation unit 3 can be provided with an earphone 11 for supplying acoustical information to the person 1.

In the embodiment shown in FIG. 3, a combined sensor/evaluation unit 6 is worn by the person 1. This combined sensor/evaluation unit 6 can include all of the components shown in FIG. 2 for the evaluation unit 3. The embodiment shown in FIG. 3 is also used to illustrate the transmission of information from the person 1 to a remote evaluation station 7. The remote evaluation station 7 can be equipped with a personal computer 7a for either evaluating the raw data, or taking appropriate actions dependent on the evaluated data supplied from the unit 6. The remote evaluation station 7 can have the capability of transmitting information back to the unit 6 (or the unit 3) in order to provide appropriate information, such as a reminder, to the person 1 if such a reminder cannot be provided by the evaluation unit 3 or 6.

In both of the embodiments shown in FIGS. 2 and 3, evaluation of the data supplied by the sensors 2 is undertaken in accordance with the time of day, such as for determining a typical motion pattern of the person 1 during the course of a day. After compiling initial data representative of a typical motion pattern, subsequently-obtained current motion data are then evaluated by analyzing specific characteristics of the current data, and/or by comparison with the typical motion pattern. The evaluation of the motion data patterns can be undertaken using a neural network in the evaluation unit 3 or 6, or at the remote evaluation station 7. The acquired current data patterns can also be utilized to update the typical data patterns which were already produced, thereby resulting in a trainable system.

The evaluation unit 3 or 6 communicates appropriate information, such as reminders, to the person 1 at appropriate times during the course of a day, so that the person 1 is informed of the necessity of undertaking particular activities at particular times. These reminders can be given periodically dependent on the time of day, or can be produced on an "as needed" basis by the trainable system.

The evaluation unit 3 or 6 can be configured so that it communicates wirelessly with a remote location, such as the remote evaluation station 7, or with another person carrying a less complicated receiver. The remote evaluation station 7 can be located, for example, at one location of a multiple residence senior citizen home, in order to receive and evaluate data from a number of persons, and to intervene as needed.

The evaluation unit 3 or 6, however, can operate completely independently, and communicate only with the person 1 who is wearing the unit 3 or 6. Wireless transmission to a remote location may not be necessary for all circumstances.

As noted above, the communication between the unit 3 or 6 and the person 1 can be accomplished in a number of ways, such as optically, acoustically or tactually. If communication takes place by means of pre-recorded voice messages, for psychological reasons it is preferable that the nature and sound of the voice is reminiscent of a person (relative or friends) with whom the person 1 is familiar. Such a voice message can be generated by a speech synthesizer or with a speech filter (vocoder) located in the evaluation unit 3 or 6. The voice messages can simply be stored in digital form in the evaluation unit 3 or 6, and activated by a signal from the remote evaluation unit 7, or the evaluation unit 3 or 6 can contain stored programs for activating the appropriate voice message dependent on the evaluation of the data from the sensors 2.

As also noted above, the sensors 2 can operate in conjunction with a number of transmitters 12 located at appropriate locations within the living environment of the person 1. Although it may be conceivable to identify the position of the person 1 by means of signals transmitted to a satellite, this is not currently practical due to power and antenna considerations. Each transmitter 12 is a mini-transmitter with its own battery. The transmitters 12 can be placed at suitable locations such as the kitchen stove, toilet or doorframes. In a known manner, these transmitters 12 emit signals which are unique for the particular location at which the transmitter 12 is placed. These signals can be emitted continuously or intermittently. Upon the approach of the person 1 to the proximity of a transmitter 12, the signal from the transmitter 12 is received by one or more of the sensors 2, and is converted into a signal supplied to the evaluation unit 3 or 6 for evaluation therein of the position of the person 1.

The sensors 2 may additionally or alternatively be temperature sensors. The temperature sensors are not for monitoring the body temperature of the person 1, but are for the purpose of monitoring the environmental temperature, since the person 1 may need to be reminded to adjust the heat or air-conditioning levels in his or her dwelling place, or an extreme temperature may indicate an emergency situation.

In instances where more intensive care of the person 1 is necessary, the sensors 2 can be connected to the body surface of the person 1. In this case, the sensors 2 may be resistance strain gauges or thermal elements or ECG electrodes. Different types of sensors can be combined to provide different data combinations. Regardless of the sensor type, all of the data emitted by each sensor 2 is supplied to the evaluation unit 3 or 6.

The evaluation unit 3 or 6 can be connectable to the telephone network for periodic downloading or interrogation of the data in the evaluation unit 3. The remote evaluation station 7 can also be capable of transmitting to the telephone of a predetermined subscriber, such as a relative of the person 1 who is to be notified in case of emergencies.

The evaluation unit 3 or 6 worn by the person 1 may, in a further embodiment, simply store the data for subsequent downloading to a stationary computer in the living environment of the person 1, or can continuously transmit the data from the sensors 2, as that data is received, to such a stationary computer. Such transmission can take place by radio signals by infrared light signals. The evaluation can then take place in this stationary computer which, by virtue of being located in the living environment of the person 1, can communicate with the person 1 via the computer display or computer speaker. Alternatively, the stationary computer in the living environment of the person 1 can, after evaluating the data, wirelessly transmit command signals back to the body-worn unit 3 or 6, which then initiates an appropriate message to the person 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A monitoring system for obtaining and evaluating data from a person, comprising:

a motion sensor adapted to be carried body-proximate by a person to be monitored, said person having a daily routine including a motion pattern, said sensor producing a sensor signal dependent on body motion comprising said motion pattern of said daily routine;

an evaluation unit adapted to be worn by said person to be monitored, said evaluation unit containing trainable means, supplied over time with said sensor signal, for learning said daily routine over time from said sensor signal and, after said daily routine has been sufficiently learned, for evaluating said signal to detect a motion of said person deviating from said motion pattern of said daily routine for identifying a non-routine condition of said person to be monitored dependent on said sensor signal; and said evaluation unit further including means for, upon identification of said non-routine condition, communicating with said person to be monitored to transmit a message perceptible only to said person to be monitored to prompt said person to alter said non-routine condition.

2. A monitoring system as claimed in claim 1 wherein said sensor is contained in said evaluation unit.

3. A monitoring system as claimed in claim 1 wherein said sensor comprises means for supplying data to said evaluation unit identifying a position of said person.

4. A monitoring system as claimed in claim 1 further comprising temperature sensor means, adapted to be carried body-proximate by said person to be monitored, for generating a temperature signal identifying a temperature of an environment in which said person is disposed and for supplying said temperature signal to said evaluation unit, and wherein said trainable means comprises means for identifying a condition of said person to be monitored dependent on said signal from said motion sensor and said temperature signal.

5. A monitoring system as claimed in claim 4 wherein said trainable means comprises means for evaluating said sensor signal from said motion sensor and said temperature signal dependent on a time of day at which said sensor signal from said motion sensor and said temperature signal are produced.

6. A monitoring system as claimed in claim 1 wherein said trainable means comprises means for evaluating said sensor signal dependent on a time of day at which said sensor signal is produced.

7. A monitoring system as claimed in claim 1 wherein said evaluation unit includes transmitter means for wireless data transmission to a location remote from said evaluation unit.

8. A monitoring system as claimed in claim 7 further comprising receiver means for receiving said data from said transmitter means.

9. A monitoring system as claimed in claim 1 wherein said means for communicating comprises a tactile stimulator.

10. A monitoring system as claimed in claim 1 wherein said means for communicating comprises means for reproduction of spoken messages.

11. A monitoring system as claimed in claim 1 wherein said at least one sensor comprises a sensor attached to a body surface of said person.

12. A monitoring system as claimed in claim 1 wherein said evaluation unit comprises means for communicating information to a telephone network.

13. A monitoring system as claimed in claim 1 further comprising a stationary computer, remote from said evaluation unit, and wherein said evaluation unit comprises means for wirelessly communicating with said stationary computer.

14. A monitoring system as claimed in claim 1 further comprising a computer remote from said evaluation unit, means for supplying data from said evaluation unit to said computer, and means in said computer for communicating with said evaluation unit to initiate generation of a message communicated to said person by said evaluation unit.

* * * * *